United States Patent [19]

Collington et al.

[11] 4,371,530
[45] Feb. 1, 1983

[54] AMINOCYCLOPENTANONE AMIDES AND PHARMACEUTICAL FORMULATION

[75] Inventors: Eric W. Collington, Welwyn; Peter Hallet, Buntingford; Christopher J. Wallis, Royston; Norman F. Hayes, Hitchin, all of England

[73] Assignee: Glaxo Group Limited, London, England

[21] Appl. No.: 279,825

[22] Filed: Jul. 2, 1981

[30] Foreign Application Priority Data

Jul. 4, 1980 [GB] United Kingdom ............... 8022048

[51] Int. Cl.³ ............... A61K 31/535; A61K 31/55; C07D 295/14
[52] U.S. Cl. ............... 424/244; 424/246; 424/248.51; 424/248.53; 424/248.54; 424/250; 424/267; 424/274; 424/275; 544/58.1; 544/58.2; 544/58.7; 544/146; 544/168; 544/379; 544/400; 546/205; 546/213; 546/233; 546/234; 548/527; 548/568; 260/239 BF; 260/330.3; 260/330.6; 542/426
[58] Field of Search ............... 544/58.2, 58.1, 58.7, 544/146, 168, 379, 400; 546/205, 213, 233, 234; 260/239 BF, 326.33, 326.35, 326.4, 330.3, 330.6; 424/244, 246, 248.51, 248.53, 248.54, 250, 267, 274, 275; 542/426

[56] References Cited

U.S. PATENT DOCUMENTS

| | | | |
|---|---|---|---|
| 4,182,903 | 1/1980 | Favara | 562/503 |
| 4,189,606 | 2/1980 | Favara | 562/455 |
| 4,265,891 | 5/1981 | Collington et al. | 424/244 |

OTHER PUBLICATIONS

Le Breton et al., *Proc. Natl. Acad. Sci. USA*, vol. 76, (1979), 4097-4100.
Orth et al., Topics in Current Chemistry, 72, 51-97, (1977).

*Primary Examiner*—Robert W. Ramsuer
*Attorney, Agent, or Firm*—Bernard, Rothwell & Brown

[57] ABSTRACT

Compounds are described of the formula

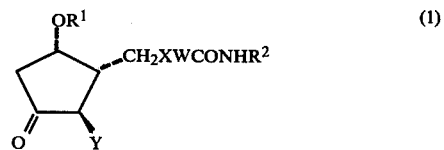

in which
$R^1$ is unsubstituted or substituted phenylalkyl, thienylalkyl or naphthylalkyl, or cinnamyl;
$R^2$ is a hydrogen atom, methyl or alkyl substituted by alkoxy or —COOH;
W is alkylene;
X is cis or trans —CH=CH— or —CH$_2$CH$_2$—; and
Y is a saturated heterocyclic amino group having 5-8 ring members;
and their salts and solvates.

These compounds inhibit blood platelet aggregation and bronchoconstriction and may be formulated for use as antithrombotic and anti-asthmatic agents.

9 Claims, No Drawings

AMINOCYCLOPENTANONE AMIDES AND PHARMACEUTICAL FORMULATION

The endoperoxides prostaglandins $G_2$ and $H_2$ and thromboxane $A_2$ are naturally occurring, reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases. Compounds in this group also have good chemical stability as compared with the parent carboxylic acids.

The invention thus provides compounds of the general formula (1)

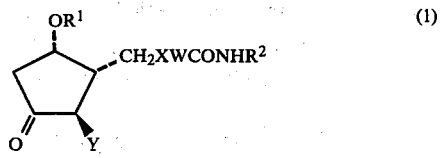

wherein $R^1$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl or phenyl (optionally substituted by $C_{1-4}$ alkyl, $C_{1-4}$ alkoxy or phenyl)], (b) thienyl [optionally substituted by $C_{1-6}$ alkyl, $C_{1-6}$ alkoxy, $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl; $R^2$ is a hydrogen atom, a methyl group, $-(CH_2)_nOR^3$ (where n is 2-5 and $R^3$ is $C_{1-4}$ alkyl) or $-CHR^4(CH_2)_m$COOH (where $R^4$ is a hydrogen atom or a methyl group and m is 0-2);

W is straight or branched $C_{1-7}$ alkylene;

X is cis or trans $-CH=CH$ or $-CH_2CH_2-$;

Y is a saturated heterocyclic amino group (attached to the cyclopentane ring via the nitrogen atom) which has 5-8 ring members and (a) optionally contains in the ring $-O-$, $-S-$, $-SO_2-$, or $-NR^5$ (where $R^5$ is a hydrogen atom, $C_{1-7}$ alkyl or aralkyl having a $C_{1-4}$ alkyl portion); and/or (b) is optionally substituted by one or more $C_{1-4}$ alkyl groups;

and the physiologically acceptable salts and solvates thereof.

The structural formulae herein are to be understood to include the enantiomers of each of the compounds concerned as well as mixtures of the enantiomers including racemates, even though the precise structure as set out only relates to one enantiomer.

The amino group Y enables the compounds to form salts with organic acids, e.g. maleates. Also, when the group $R^2$ is $-CHR^4(CH_2)_m$COOH, salts may be formed with bases. Examples of such salts are alkali metal (e.g. sodium), alkaline earth metal (e.g. calcium) and amine (e.g. piperazine) salts.

Examples of $R^2$ groups of the types $-(CH_2)_n$ $OR^3$ and $-CHR^4(CH_2)_m$COOH are $-(CH_2)_2OCH_3$, $-(CH_2)_3OCH_3$ and $-CH_2COOH$. $R^2$ is preferably a hydrogen atom.

The W group is preferably $-CH_2CH_2CH_2-$.

X is preferably a cis $-CH=CH-$ group.

The heterocyclic amino group Y may for example have a 5, 6 or 7-membered ring, e.g. pyrrolidino, piperidino, morpholino, piperazino, thiamorpholino, 1,1-dioxothiamorpholino, homomorpholino and hexamethyleneimino. Examples of the optional substituents which may be present on a second nitrogen atom in the ring are methyl, ethyl and benzyl. The carbon atoms of the heterocyclic rings may for example be substituted by methyl or ethyl.

Compounds in which Y is a morpholino or piperidino group are preferred.

When $R^1$ is a substituted alkyl group, the alkylene portion may for example contain 1-3 carbon atoms and is preferably a methylene group.

$R^1$ is preferably a phenylalkyl group in which the alkyl portion contains 1-3 carbon atoms and the phenyl group is substituted by thienyl or phenyl (which phenyl group may itself be optionally substituted by $C_{1-4}$ alkyl or $C_{1-4}$ alkoxy) or is a phenylthienylalkyl group in which the alkyl portion contains 1-3 carbon atoms.

Particularly preferred $R^1$ groups are benzyl groups in which the phenyl group carries (preferably in the para-position) a phenyl, tolyl or methoxyphenyl substituent.

Thus a particularly preferred group of compounds has the formula (1) in which:

W is $-CH_2CH_2CH_2-$,

X is cis $-CH=CH-$,

Y is morpholino or piperidino, $R^1$ is benzyl in which the phenyl group is substituted by phenyl, tolyl or methoxyphenyl, and $R^2$ is a hydrogen atom, and the physiologically acceptable salts and solvates thereof.

Compounds of formula (1) inhibit blood platelet aggregation and bronchoconstriction. To determine inhibition of blood platelet aggregation, starved guinea-pigs are dosed orally with the compound to be tested in a suitable vehicle. Platelet rich plasma is prepared from each animal and aggregation to a range of collagen concentrations is measured after the method of Born (Nature 194, 927-929, (1962)). Collagen concentration-effect curves for each sample of plasma are calculated and results are expressed as the shift of the curves following treatment with the compound.

The ability of the compounds of the invention to inhibit bronchoconstriction is determined in the anaesthetized guinea pig by measuring their effect on the dose response curve of the bronchoconstrictor [1R-[1α, 4α, 5β(Z), 6α(1E, 3S*)]]-7-[6-(3-hydroxy-1-octenyl)-2-oxabicyclo-[2,2,1]hept-5-yl]-5-heptenoic acid (U-46619).

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebal vascular disease including transient ischaemic attacks, stroke, pulmonary embolism, diabetic retinopathy, post operative thrombosis, angina and myocardial infarction. They may be formulated in conventional manner for use, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

The compounds are preferably administered orally, for example in amounts of 0.05 and 10 mg/kg body weight, 1 to 4 times daily. For use in the treatment of asthma, the compounds may be used in combination with other anti-asthmatic agents. The precise dose administered will of course depend on the age and condition of the patient.

Suitable methods for preparing compounds of formula (1) are described below, the groups $R^1$, $R^2$, W, X and Y being as defined above except where otherwise indicated.

(a) Compounds of formula (1) may be prepared by oxidising a corresponding hydroxy compound, e.g. a compound of formula (2)

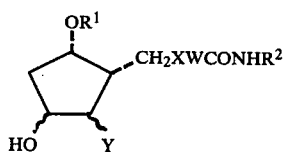

(2)

Suitable methods of oxidation include using a $Cr^{vi}$ oxidising reagent in a suitable solvent, e.g. chromic acid in acetone (e.g. Jones reagent, preferably used in the presence of a diatomaceous silica such as Celite) or $CrO_3$ in pyridine. These reagents are for example used at temperatures of $-20°$ to room temperature.

Other important methods include using an activated sulphur reagent, e.g. (i) N-chlorosuccinimidedimethylsulphide complex in a suitable solvent (e.g. toluene or dichloromethane) at temperatures of for example $-25°$ to $25°$, preferably at $0°-5°$, (ii) a dialkylsulphoxide (e.g. dimethylsulphoxide) activated by a suitable electrophilic reagent (such as oxalyl chloride, acetyl bromide or thionyl chloride) in a suitable solvent (e.g. toluene or dichloromethane), e.g. at $-70°$ to $-20°$; dicyclohexylcarbodiimide can also be used as the electrophilic reagent (preferably in the presence of $CF_3COOH$ or its pyridinium salt) at for example $-10°$ to room temperature, using the same solvents, or (iii) pyridine-$SO_3$ complex in dimethylsulphoxide, preferably at $0°$ to room temperature. Method (ii) should not be used where $R^2$ is a hydrogen atom. When Y is in the $\alpha$-configuration conditions should be chosen to effect epimerisation after oxidation e.g. by using a $Cr^{VI}$ oxidising agent.

The starting materials of formula (2) may be prepared from the parent carboxylic acids of formula (3)

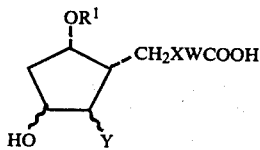

(3)

(or a $C_{1-6}$ alkyl ester thereof) using conventional methods for converting acids into amides.

For example, a reactive derivative of an acid of formula (3) may be treated with ammonia or an amine $H_2NR^2$ in a suitable solvent, e.g. acetone or acetonitrile. The reactive derivative is conveniently a mixed anhydride of the acid (3), formed for example by treatment of the acid (3) with a chloroformate in the presence of a suitable base, e.g. triethylamine or pyridine.

The chloroformate may for example be a $C_{1-6}$ alkyl (e.g. methyl, ethyl, isobutyl, sec-butyl, t-butyl, isopropyl or isoamyl), aryl (e.g. phenyl) or aralkyl (e.g. benzyl) chloroformate.

Alternatively, the reactive derivative may be an imidazolide, formed for example by treatment of the acid (3) with 1,1'-carbonyldiimidazole. The ring hydroxy group should be protected during the latter reaction, e.g. in the form of a tetrahydro-2H-pyran-2-yloxy or t-butyldimethyl-silyloxy group. These protecting groups can subsequently be removed by acid hydrolysis.

In another method, an ester of an acid of formula (3) may for example be heated (e.g. at $100°-130°$ C.) with ammonia or an amine $H_2NR^2$, optionally using a solvent such as an alcohol.

The preparation of many of the acids of formula (3) and esters thereof in which Y is in the $\beta$-position and the ring hydroxy group is in the $\alpha$-position is described in British Patent Specification No. 2028805A. The same general methods may be used to prepare all of these compounds using starting materials containing the required $R^1$ group.

Acids of formula (3) and esters thereof in which Y and the ring hydroxy groups are both in the $\alpha$-configuration may also be prepared by the methods described in British Patent Specification No. 2028805A, using a norbornanone of formula (4) as starting material:

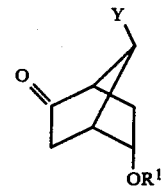

(4)

The norbornanones of formula (4) may be prepared by the following sequence:

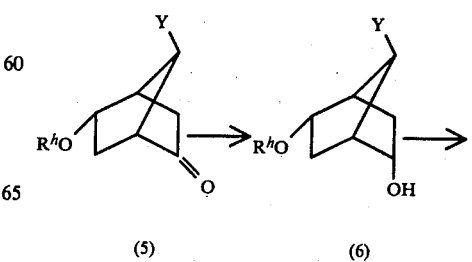

-continued

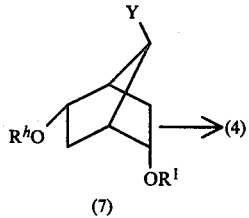

($R^h$ above represents a hydroxyl protecting group). Thus the norbornanone (5) is first reduced (e.g. with NaBH$_4$) to the alcohol (6) into which the $R^1$ group is then introduced (e.g. by reaction with $R^1L$, where L is a leaving group, e.g. halogen or tosylate) to give the compound (7). The protecting group ($R^h$) is then removed and the hydroxy group oxidised (e.g. as described for process (a)) to give the norbornanone (4).

The norbornanones (5) may be prepared by the general method described in British Patent Specification No. 2028805A.

Compounds of formula (3) and esters thereof in which Y is in the α-configuration and the ring hydroxy group is in the β-configuration may be prepared by epimerising the corresponding compound in which the ring hydroxy group is in the α-position. This may for example be effected with triphenylphosphine in the presence of an acid (e.g. formic or benzoic acid) and (C$_2$H$_5$OOC.N)$_2$ at room temperature, followed by treatment with a base (e.g. K$_2$CO$_3$) in a solvent such as methanol.

Acids of formula (3) and esters thereof in which both Y and the ring hydroxy group are in the β-position may be prepared from the corresponding compound of formula (3) in which the hydroxy group is in the α-position, by oxidation of the hydroxy group (e.g. by the method of process (a)) followed by reduction (e.g. with lithium tri-sec-butyl borohydride).

(b) Compounds of formula (1) may also be prepared by selective reduction of a corresponding compound of formula (1) in which X is an acetylene group. Suitable methods of reduction include using hydrogen in the presence of a catalyst, e.g. palladium on a support (e.g. CaCO$_3$ or BaSO$_4$) and poisoned for example by lead or pyridine. Suitable solvents include ethyl acetate or methanol.

The acetylenes required as starting materials for this reaction may be prepared from an amide of formula (8) in which X is —CH=CH—

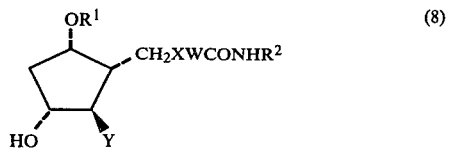

The hydrochloride of an amide (8) is first brominated to give the corresponding compound in which X is —CHBr.CHBr—, e.g. using bromine in CH$_2$Cl$_2$ at 0° C.

The dibromo compound is then dehydrobrominated to form the acetylene group, for example in two stages, using potassium t-butoxide first at 0° and then at room temperature. Oxidation, for example as described for process (a), then gives the required starting material.

(c) Compounds of formula (1) may also be prepared by amidation of a reactive derivative of the corresponding carboxylic acid. This reaction can be performed as described above for the preparation of amides of formula (2) from acids of formula (3). Thus for example, a reactive derivative of an acid (9)

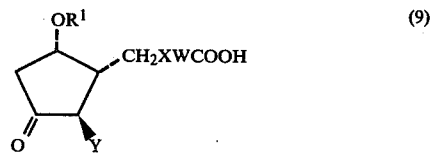

(for example, an anhydride or imidazolide as described above) may be reacted with ammonia or an amine H$_2$NR$^2$.

The acids of formula (9) may be prepared by oxidation of the corresponding acid of formula (3) or a protected derivative thereof e.g. a trialkylsilyl ester, for example as described for process (a).

(d) Compounds of formula (1) in which X is —CH$_2$CH$_2$— may be prepared by catalytic hydrogenation of a corresponding compound in which X is —CH=CH—, using a catalyst such as palladium oxide.

(e) Salts of compounds of formula (1) may be prepared by treating an amide of formula (1) with an acid, or when the group $R^2$ is —CHR$^4$(CH$_2$)$_m$COOH a base, in a suitable solvent such as ether.

The following examples illustrate the invention. Temperatures are in °C. Drying was effected with anhydrous MgSO$_4$. 'Hyflo' is a filtration aid. The following abbreviations are used: TLC—thin layer chromatography on silica, GLC—gas/liquid chromatography, EA—ethyl acetate, THF—tetrahydrofuran, PE—petroleum ether (b.p. 40°-60° C.), DMSO—dimethylsulphoxide, DMF—dimethylformamide, Dibal—diisobutyl aluminium hydride, PTSA—p-toluenesulphonic acid.

Chromatography was carried out using silica gel except where otherwise stated. The following abbrevations define the eluent used for the chromatography and TLC:

(A) 85:15 EA-methanol
(B) 9:1 ether-methanol
(C) 4:1 ether-methanol
(D) 9:1 EA-methanol
(E) 85:15 ether-methanol
(F) 95:5 ether-methanol
(G) 92:8 ether-methanol
(H) 6:4 ether-methanol
(I) 97:3 ether-methanol
(J) 88:12 ether-methanol
(K) 4:1 ether-PE
(L) ether
(M) 96:4 ether-methanol
(N) 7:3 ether-methanol
(O) 1:1 ether-methanol
(P) 95:5 EA-methanol
(Q) 9:1 PE(b.p.60°-80°)-EA The preparations of Intermediates 1-3 are described in British Patent Specification No. 2 028 805 A.

INTERMEDIATE 1

[1α(Z),2β,3α,5α]-(±)-7-[5-[[(1,1'-Biphenyl)-4-yl]methoxy]-3-hydroxy-2-(4-morpholinyl)cyclopentyl]-5-heptenoic acid

INTERMEDIATE 2

[1α(Z),2β,3α,5α]-(±)-Methyl 7-[5-[[(1,1-Biphenyl)-4-yl]methoxy]-3-hydroxy-2-(1-piperidinyl)cyclopentyl]-5-heptenoate

INTERMEDIATE 3

[1α(Z),2β,5α]-(±)-7-[5-[[(1,1'-Biphenyl)-4-yl]methoxy]-2-(4-morpholinyl)-3-oxocyclopentyl]-5-heptenoic acid

INTERMEDIATE 4a

[4'-Methyl-(1,1'-biphenyl)-4-yl]methanol

4-Methyl-(1,1'-biphenyl)-4-carboxylic acid, methyl ester (1.43 g) in ether (25 ml) and THF (25 ml) was added over 5 min to LiAlH₄ (420 mg) in ether (25 ml). The mixture was stirred at room temperature for 1h and then cooled in ice. Aqueous NaOH (1 M, 2.1 ml) was added and after stirring (15 min) excess anhydrous Na₂SO₄ was added. The mixture was filtered and the filtrate evaporated to give a solid. Crystallisation from cyclohexane-methanol gave the title compound (1.04 g) m.p. 128°–31°.

INTERMEDIATE 4b

4-Bromomethyl-4'-methyl (1,1'-biphenyl)

To a cold (0°) solution of Intermediate 4a (0.917 g) in dry CH₂Cl₂ (14 ml) was added PBr₃ (0.29 ml). After stirring for 1h at 0°, 8% NaHCO₃ solution (30 ml) was added and the layers separated. The aqueous layer was extracted with CH₂Cl₂ (2×30 ml), dried and evaporated to give a solid (0.99 g). Crystallisation from PE (b.p. 60°–80°) afforded the title compound (0.91 g) m.p. 100°–102°.

INTERMEDIATE 4c

[1α(Z),2β,3α,5α]-(±)-Methyl 7-[3-Hydroxy-5-[[4'-methyl(1,1'-biphenyl)-4-yl]methoxy]-2-(4-morpholinyl)cyclopentyl]-5-heptenoate A solution of [1α(Z),2β,3α,5α]-methyl 7-[5-hydroxy-2-(4-morpholinyl)-3-[(tetrahydro-2H-pyran-2-yl)oxy]cyclopentyl]-5-heptenoate (0.43 g) and Intermediate 4b (0.68 g) in dry DMF (6 ml) was stirred at 0° under nitrogen during the addition of NaH (0.08 g, 80% dispersion in oil). After 4h at 20°, the mixture was carefully poured into saturated aqueous NH₄Cl (70 ml) and extracted with ether (3×40 ml). The combined extracts were dried, filtered and evaporated, and the residue then stirred with 5% methanolic sulphuric acid (20 ml) at 20° for 2h. The mixture was poured into 8% NaHCO₃ solution (100 ml), extracted with ether (3×50 ml), dried, evaporated and the residue purified by chromatography (P). The title compound was crystallised from ether-PE as needles (0.14 g), m.p. 75°–77°.

INTERMEDIATE 4

[1α(Z),2β,3α,5α]-(±)-7-[3-Hydroxy-5-[[4'-methyl(1,1'-biphenyl)-4-yl]methoxy]-2-(4-morpholinyl)cyclopentyl]-5-heptenoic acid A suspension of Intermediate 4c (0.44 g) in methanol (2 ml) and water (4 ml) containing KOH (0.35 g) was stirred at room temperature for 7h. The methanol was removed and the residue further diluted with water (75 ml), washed with ether (75 ml) and then carefully acidified to pH 6 with 2 N hydrochloric acid. Extraction with ether (4×50 ml) followed by drying and evaporation gave the title compound (0.35 g) as a foam. IR (CHBr₃) 3500, 3200(br.), 1730, 1700 cm⁻¹. TLC (D) R_f 0.25.

INTERMEDIATE 5a (endo,anti)-(±)-6-[[4'-Methoxy(1,1'-biphenyl)-4-yl]methoxy]-8-(4-morpholinyl)-2-oxabicyclo[3.2.1]octan-3-one 4-Bromoanisole (7.48 g) in ether (30 ml) was added to Mg turnings (1.06 g) in THF (40 ml) containing a small iodine crystal. After 0.5h an exothermic reaction took place which was moderated by water bath cooling. The resultant mixture was stirred at 20° for a further 0.5h and then added, under nitrogen, to a stirred, cooled (5°) solution of anhydrous ZnBr₂ (9.0 g) in THF (40 ml) and stirred for 1h.

Dibal (1 M in hexane; 5.72 ml) was added dropwise to a suspension of bis(triphenylphosphine)palladium chloride (2.0 g) in THF (20 ml). After stirring for 5 min. a solution of Intermediate 8d (2.38 g) in THF (35 ml) was added followed after a further 5 min. by the solution of 4-methoxyphenylzinc bromide described above. The resultant mixture was stirred under nitrogen at 20° for 18h. The solvent was then removed in vacuo, NH₄Cl solution (150 ml) added and the mixture extracted with EA (3×100 ml). Evaporation of the dried extracts gave an oil which was chromatographed (EA) to give the title compound as a solid. Crystallisation from EA-PE (b.p. 60°–80°) gave material (1.58 g) of m.p. 123°–125°.

INTERMEDIATE 5b (1α,2β,3α,5α)-(±)-3-Hydroxy-5-[[4'-methoxy(1,1'-biphenyl)-4-yl]methoxy]-2-(4-morpholinyl)cyclopentane acetaldehyde A solution of Intermediate 5a (1.6 g) in CH₂Cl₂ (25 ml) at −70° under dry nitrogen was stirred during the addition of Dibal (1 M in hexane, 8.7 ml). After 1.5h at −70°, methanol (25 ml) was carefully added and the mixture was then allowed to rise to ambient temperature whereupon stirring was continued for 18h. The mixture was filtered through 'Hyflo' and the filtrate evaporated to give the title compound as a foam (1.68 g). IR (CHBr₃) 3580/3560(br), 1715, 1240, 1040 cm⁻¹.

INTERMEDIATE 5

[1α(Z),2β,3α,5α]-(±)-7-[3-Hydroxy-5-[[4'-methoxy(1,1'-biphenyl)-4-yl]methoxy]-2-(4-morpholinyl)cyclopentyl]-5-heptenoic acid To a solution of potassium t-butoxide (2.28 g) in THF (15 ml) under dry nitrogen was added (4-carboxybutyl)triphenylphosphonium bromide (4.5 g). After 15 min at 20° a solution of Intermediate 5b (1.6 g) in THF was added and stirring continued for a further 1h. Water (2 ml) was added and the THF removed in vacuo. The residue was taken up into water (100 ml), basified (pH 10) with NaOH solution and washed with ether (2×75 ml). The aqueous layer was adjusted to pH 6 with 2 N hydrochloric acid, extracted with ether (5×75 ml), dried, evaporated and re-dissolved in EA (25 ml) and ether (40 ml). To the solution was added an excess of ethereal hydrogen chloride solution followed by cooling until crystallisation occurred. Filtration and purification from EA-methanol gave the title compound (1.2 g) as its hydrochloride. m.p. 164°–166°.

INTERMEDIATE 6a

4-(1,3-Dioxolan-2-yl)-2-phenylthiophene

A solution of 5-bromo-3-thiophenecarboxaldehyde (32.5 g) in benzene (500 ml) was treated with PTSA (0.323 g) and ethylene glycol (21.1 g), and the mixture heated under reflux in a Dean and Stark apparatus until the theoretical volume of water had been removed. After cooling the mixture was washed with water, (2×) then brine, dried, filtered and concentrated, and the residue distilled (b.p. 96°–100° at 0.4 mm) to give the title compound as an oil (24 g).

Analysis Found: C, 35.8; H, 3.0; $C_7H_7BrO_2S$ requires: C, 35.7; H, 3.0%.

INTERMEDIATE 6b

5-Phenyl-3-thiophenecarboxaldehyde

A solution of phenylmagnesium chloride in THF (82.94 ml, 2.39 M) was added to a stirred solution of $ZnBr_2$ (44.6 g) in dry THF (350 ml) under nitrogen. The mixture was stirred at room temperature for 15 min.

Dibal (9.91 ml, 1 M) in hexane solution was added dropwise to a stirred mixture of triphenylphosphine (10.39 g) and nickel acetoacetonate (2.55 g) in dry THF (160 ml) under nitrogen. A solution of Intermediate 6a (23.3 g) in dry THF (150 ml) was added after 10 min. The solution containing the organozinc reagent was then added dropwise and the mixture was stirred for 1h.

2 N Hydrochloric acid (400 ml) was added at 0° and the mixture was stirred at room temperature for 0.5h. The two layers were separated and the aqueous layer was extracted with ether (2×400 ml), washed with $NaHCO_3$ solution and brine and then dried. Solvent removal in vacuo gave a solid (32.8 g) which was chromatographed (Q) to give the title compound (13.35 g), m.p. 64°–65° (from PE (b.p. 60°–80°)).

INTERMEDIATE 6c

5-Phenyl-3-thiophenemethanol

A stirred solution of Intermediate 6b (12 g) in methanol (120 ml) was treated with $NaBH_4$ (1.82 g) at room temperature for 15 min. The mixture was cooled to 0° and treated with $NH_4Cl$ solution (200 ml), followed by water (200 ml) and ether (400 ml). The ether extract was separated and the aqueous phase further extracted with ether (400 ml). The combined extracts were washed with brine, dried, filtered and evaporated to afford the title compound as a solid (11.5 g), m.p. 92°–93°.

INTERMEDIATE 6d

4-(Bromomethyl)-2-phenylthiophene

A solution of Intermediate 6c (4 g) in $CH_2Cl_2$ (70 ml) at 0° was treated with phosphorus tribromide (1.32 ml) in $CH_2Cl_2$ (5 ml). After 10 min. 8% $NaHCO_3$ solution (70 ml) was added and the layers were separated. The aqueous phase was extracted with $CH_2Cl_2$ (40 ml). The combined organic layers were washed with brine (50 ml), dried and evaporated to give the title compound (4.87 g). TLC (L) $R_f$ 0.58.

INTERMEDIATE 6e

[1α(Z),2β,5α]-(±)-Methyl 7-[3-Hydroxy-2-(4-morpholinyl)-5-[(2-phenylthien-4-yl)methoxy]cyclopentyl]-5-heptenoate Sodium hydride (0.88 g, 50% dispersion in oil) was added to a stirred solution of Intermediate 6d (4.6 g) and [1α(Z),2β,3α,5α]-(±)-methyl-7-[5-Hydroxy-2-(4-morpholinyl)-3-[(tetrahydro-2H-pyran-2-yl)oxy]cyclopentyl]-5-heptenoate (2.5 g) in dry DMF (15 ml) at 0°. After 1h at ambient temperature ammonium chloride solution (100 ml) was added at 0° and the pH was adjusted to 6.5 using $KH_2PO_4$. The mixture was extracted with ether (3×100 ml) and the combined extracts were washed with water (2×200 ml), dried and evaporated. The residue was stirred with 9:1 methanol-conc. sulphuric acid (20 ml) for 3h. 8% $NaHCO_3$ solution (100 ml) was added and the mixture was extracted with EA (3×70 ml). The combined extracts were washed with brine (100 ml), dried and evaporated and the residue was purified by chromatography (B) to give the title compound as an oil (0.98 g).

IR ($CHBr_3$) 3590, 1728 $cm^{-1}$.

INTERMEDIATE 6

[1α(Z),2β,3α,5α]-(±)-7-[3-Hydroxy-2-(4-morpholinyl)-5-[(2-phenylthien-4-yl)methoxy]cyclopentyl]-5-heptenoic acid A solution of Intermediate 6e (0.9 g) in methanol (10 ml) and 2 N NaOH solution (5 ml) was stirred at ambient temperature for 3h. The methanol was removed in vacuo and the residual solution was adjusted to pH 6.5 with $KH_2PO_4$. The mixture was extracted with EA (3×15 ml) and the combined extracts were washed with brine (10 ml), dried and evaporated to give the title compound as a foam (0.84 g).

TLC (C) $R_f$ 0.48

INTERMEDIATE 7a

(3aα,4α,5β,6aα)-(±)-Hexahydro-5-hydroxy-4-(4-thiomorpholinyl)-2H-cyclopenta(b)furan-2-one, S-dioxide, hydrochloride A solution of (endo, anti)-(±)-6-(phenylmethoxy)-8-(4-thiomorpholinyl)-2-oxabicyclo[3.2.1]octan-3-one, S-dioxide (10 g) in ethanol (60 ml) and water (40 ml) containing concentrated hydrochloric acid (40 ml) was hydrogenated over pre-reduced 10% palladium oxide on charcoal (5 g, 50% dispersion in water) in ethanol (40 ml). The mixture was filtered and the filtrate evaporated in vacuo to give the title compound as a solid (8.55 g), m.p. above 230° (dec.) (from water-ethanol).

INTERMEDIATE 7b

(3aα,4α,5β,6aα)-(±)-Hexahydro-5-[(tetrahydro-2H-pyran-2-yl)oxy]-4-(4-thiomorpholinyl)-2H-cyclopenta(b)furan-2-one, S-dioxide Dihydropyran (3.1 ml) was added to a stirred solution of the free base of Intermediate 7a (1.56 g) and PTSA (1.17 g) in dry DMF (30 ml) at −10°. The mixture was allowed to reach ambient temperature and stirring continued for 18h, whereupon it was poured into saturated aqueous $NaHCO_3$ solution (50 ml), extracted with EA (4×100 ml), washed with water, dried, filtered and concentrated. The residue was chromatographed (F) to give the title compound as a viscous oil (1.89 g). IR ($CHBr_3$) 1762 $cm^{-1}$.

INTERMEDIATE 7c (3aα,4α,5β,6aα)-(±)-Hexahydro-5-[(tetrahydro-2H-pyran-2-yl)oxy]-4-(4-thiomorpholinyl)-2H-cyclopenta(b)furan-2-ol, S-dioxide Dibal (1.43 M in hexane; 3.9 ml) was added dropwise to a stirred solution of Intermediate 7b (1 g) in dry $CH_2Cl_2$ (15 ml) under nitrogen at $-70°$. After 15 min. methanol (15 ml) was cautiously added and the mixture allowed to warm to ambient temperature. After 1h the mixture was filtered and the filtrate was evaporated to give the title compound as an oil (0.95 g).

Analysis found: C, 53.2; H, 7.6; N, 3.5; $C_{16}H_{27}NO_6S$ requires: C, 53.2; H, 7.5; N, 3.9%.

INTERMEDIATE 7

[1α(Z),2β,3α,5α]-(±)-Methyl 7-[5-Hydroxy-3-[(tetrahydro-2H-pyran-2-yl)oxy]-2-(4-thiomorpholinyl)cyclopentyl]-5-heptenoate, S-dioxide To a stirred solution of potassium t-butoxide (1.12 g) in dry THF (10 ml) under dry nitrogen was added (4-carboxybutyl)triphenylphosphonium bromide (2.21 g) and the mixture stirred at 22° for 15 min., whereupon a solution of Intermediate 7c (0.9 g) in THF (5 ml) was added and stirring continued for a further 30 min. Water (50 ml) was added and the mixture extracted with EA (3×25 ml). The aqueous phase was adjusted to pH 6.5 with $KH_2PO_4$ solution and then extracted with EA (3×30 ml), washed with brine, dried and treated with ethereal diazomethane. Concentration gave an oil which was chromatographed (F) to give the title compound (0.63 g).

Analysis Found: C, 57.8; H, 8.3; N, 2.9; $C_{22}H_{37}NO_7S$ requires: C, 57.5; H, 8.1; N, 3.1%.

INTERMEDIATE 8a (endo,anti)-(±)-7-(4-Morpholinyl)-5-[(tetrahydro-2H-pyran-2-yl)oxy]bicyclo[2.2.1]heptan-2-one Morpholine (76 ml) was added dropwise over 15 mins to a stirred solution of (exo,endo)-(±)-2-bromo-3-[(tetrahydro-2H-pyran-2-yl)oxy]bicyclo[3.2.0]heptan-6-one (100.8 g) in acetone (500 ml) at 0°. After 2h at 5° the mixture was stirred at 20° for 18h and then filtered. Evaporation of the filtrate gave an oil which was taken into ether (350 ml), filtered and washed (water, 2×100 ml). The ethereal solution was dried, filtered and evaporated to give the title compound as a solid. Purification from PE gave material (85.5 g) of m.p. 86°–88°.

INTERMEDIATE 8b (endo,anti)-(±)-5-Hydroxy-7-(4-morpholinyl)bicyclo[2.2.1]heptan-2-one, hydrochloride To a stirred solution of Intermediate 8a (96.4 g) in methanol (600 ml) was added an ethereal solution of HCl (240 ml) and the mixture stirred at 20° for 2.5h (pH 1.5–2). Filtration followed by evaporation of the filtrate gave and oil which solidified on trituration with EA (2×200 ml). Coloured impurities were removed by extraction with boiling isopropanol to leave the title compound as a solid (70.6 g), m.p. 181°–182°.

INTERMEDIATE 8c (endo, anti)-(±)-5-(4-Bromophenylmethoxy)-7-(4-morpholinyl)bicyclo[2.2.1]heptan-2-one Aqueous NaOH solution (10 N; 200 ml) was added to a solution of the free base of Intermediate 8b (21.1 g), benzyltriethylammonium chloride (4 g) and 4-bromobenzyl bromide (27.5 g) in $CH_2Cl_2$ (400 ml) and the mixture stirred vigorously for 4h. A further portion of 4-bromobenzylbromide (9 g) was then added and stirring continued for 68h. Water (200 ml) was added and the layers separated. The aqueous layer was extracted with EA (2×75 ml), washed with water, dried and evaporated to give an oil (48 g) which solidified on standing. Excess alkylating agent was removed by trituration with PE (b.p. 60°–80°) and crystallisation from EA-PE (b.p. 60°–80°) then gave the title compound (34.1 g) as a solid, m.p. 130°–131°.

INTERMEDIATE 8d (endo,anti)-(±)-6-(4-Bromophenylmethoxy)-8-(4-morpholinyl)-2-oxabicyclo[3.2.1]octan-3-one Intermediate 8c (13.2 g) in acetic acid (110 ml) and water (55 ml) containing $CH_3COONa.3H_2O$ (23.7 g) was cooled (ca. 5°–10°) and stirred during the dropwise addition of peracetic acid (6.1 M; 28.5 ml). The resulting solution was stirred at 20° for 48h when 10% $Na_2SO_3$ solution (200 ml), was added, maintaining the temperature of the mixture at 10°–15°. After 1.5h solvents were removed in vacuo at 35°, the residue taken into water (150 ml) and basified to pH 9 with $Na_2CO_3$ solution. Extraction with EA (3×200 ml) followed by drying and evaporation gave a solid which crystallised from EA to give the title compound (5.49 g), m.p. 154°–156°.

INTERMEDIATE 8e (endo,anti)-(±)-[4-(Thien-2-yl)phenylmethoxy]-8-(4-morpholinyl)-2-oxabicyclo[3.2.1]octan-3-one The Grignard reagent from 2-bromothiophene (4.1 g) and magnesium (0.7 g) was prepared in dry ether (50 ml); the exothermic reaction was moderated by cold water cooling. The reagent was added to a stirred, cooled (5°) solution of anhydrous $ZnBr_2$ (5.6 g) in THF (30 ml) and stirred for 1h.

Dibal (1 M in hexane; 3.6 ml) was added dropwise to a suspension of bis(triphenylphosphine)palladium chloride (1.25 g) in THF (20 ml). After 5 min. a solution of Intermediate 8d (1.5 g) was added followed after a further 5 min. by the solution of thienylzinc bromide described above. The mixture was stirred under nitrogen for 16h at ambient temperature then poured into ammonium chloride solution (150 ml) and extracted with EA (3×100 ml). Evaporation of the dried extracts gave an oil which was purified by chromatography, EA-PE (b.p. 60°–80°) (1:2, 1:1 and 2:1 successively), to give the title compound as a solid, m.p. 216°–217°.

INTERMEDIATE 8f (1α,2β,3α,5α)-(±)-3-Hydroxy-2-(4-morpholinyl)-5-[4-(thien-2-yl)phenylmethoxy]cyclopentane acetaldehyde Dibal (1 M in hexane; 8 ml) was added dropwise to a stirred solution of Intermediate 8e (0.55 g) in dry $CH_2Cl_2$ (20 ml) under nitrogen at −70°. After 4h methanol (10 ml) was cautiously added and the mixture allowed to warm to ambient temperature. After 16h the mixture was filtered and the filtrate was evaporated to give the title compound (0.55 g).

TLC (P) $R_f$ 0.3

INTERMEDIATE 8

[1α(Z),2β,3α,5α]-(±)-7-[3-Hydroxy-2-(4-morpholinyl)-5-[4-(thien-2-yl)phenylmethoxy]cyclopentyl]-5-heptenoic acid To a solution of potassium t-butoxide (1.54 g) in THF (30 ml) under dry nitrogen was added (4-carboxybutyl)-triphenylphosphonium bromide (2.9 g). After 10 min. at 20° a solution of Intermediate 8f (0.55 g) in THF (30 ml) was added and stirring was continued for 5h. The mixture was poured into ammonium chloride solution and extracted with ether. The dried extracts were evaporated and the residue was purified by chromatography (PE) followed by (D) to give the title compound (0.44 g).

IR (Neat) 3360, 1710 $cm^{-1}$

INTERMEDIATE 9a (endo,anti)-(±)-7-Azido-5-hydroxybicyclo[2.2.1]heptan-2-one

A solution of (exo,endo)-(±)-3-acetoxy-2-bromobicyclo[3.2.0]heptan-6-one (50 g) and potassium t-butoxide (27.25 g) in THF (1.5 l) was stirred at −75° for 1h. The solution was allowed to warm to 0° and a solution of sodium azide (16.45 g) in water (600 ml) was added and stirring continued at 20° for 18h.

The two layers were separated and ether was added to the organic layer which was washed with water (2×250 ml). The combined aqueous layers were extracted with ether (2×250 ml). The combined organic layers were dried and evaporated to give a gum (28.1 g). A solution of the gum in methanol (225 ml) was stirred with $K_2CO_3$ (18.37 g) for 3.5h at room temperature. The mixture was filtered and the filtrate was evaporated in vacuo to give a solid which was taken into ether (150 ml) and washed with water (150 ml). The aqueous layer was extracted with ether (3×125 ml) and the combined organic layers were dried and evaporated to give an oil (24.5 g) which was chromatographed on silica. Elution with 2:1 ether-PE gave an oil (18.7 g) which was triturated with ether to give the title compound as a solid (14.6 g), m.p. 72°–74°.

INTERMEDIATE 9b (3aα,4α,5β,6aα)-(±)-4-Azido-hexahydro-5-hydroxy-2H-cyclopenta(b)furan-2-one 40% Peracetic acid (64.35 ml) was added to a cooled (0°) stirred solution of Intermediate 9a (12.9 g) and sodium acetate (31.2 g) in acetic acid (155 ml) and water (15.5 ml) and the resulting solution then stirred at ambient temperature for 24h. Excess $Na_2SO_3$ solution was added to the cooled solution and stirring continued for 1h. After evaporation in vacuo the residue was dissolved in 5 N NaOH solution (400 ml) with cooling and the solution stirred for 0.5h. Concentrated hydrochloric acid (30 ml) was added with cooling and the solution was continuously extracted with $CH_2Cl_2$ (600 ml) for 18h. The organic extracts were washed with 2 N $Na_2CO_3$ solution (100 ml) and brine (100 ml), dried and evaporated to give a solid (3.5 g). A portion (1 g) was recrystallised from ether-PE (b.p. 60°–80°) to give the title compound (816 mg), m.p. 73°–74°.

INTERMEDIATE 9c (3aα,4α,5β,6aα)-(±)-4-Azido-hexahydro-5-[(tetrahydro-2H-pyran-2-yl)oxy]-2H-cyclopenta(b)furan-2-one Dihydropyran (6.1 ml) was added to a cold (−20°) stirred solution of PTSA (0.685 g) and Intermediate 9b (6.63 g) in $CH_2Cl_2$ (35 ml). After 2h at −20° the mixture was poured into 8% $NaHCO_3$ solution (300 ml). The organic layer was separated and the aqueous layer extracted with $CH_2Cl_2$ (3×100 ml). The combined extracts were washed with brine (200 ml), dried and evaporated in vacuo to give an oil (13.23 g) which was purified by chromatography on silica. Elution with 2:1 ether-PE (b.p. 60°–80°) gave the title compound as an oil (5.39 g). IR (Neat) 2100, 1780 $cm^{-1}$.

INTERMEDIATE 9d (3aα,4α,5β,6aα)-(±)-4-Amino-hexahydro-5-[(tetrahydro-2H-pyran-2-yl)oxy]-2H-cyclopenta(b)furan-2-one A solution of Intermediate 9c (28.4 g) in ethanol (175 ml) was hydrogenated at atmospheric pressure over pre-reduced 10% palladium oxide on charcoal (5.3 g) at 20° for 24h. The mixture was filtered ('Hyflo') and the filtrate evaporated to give an oil (24.1 g). IR ($CHBr_3$) 3370, 3300, 1762 $cm^{-1}$.

INTERMEDIATE 9e (3aα,4α,5β,6aα)-(±)-Hexahydro-5-[(tetrahydro-2H-pyran-2-yl)oxy]-4-(4-thiomorpholinyl)-2H-cyclopenta(b)furan-2-one A mixture of Intermediate 9d (6 g), anhydrous $NaHCO_3$ (5.2 g), NaI (9.72 g) and bis-(2-chloroethyl)sulphide (5.15 g) in acetonitrile (250 ml) was heated under reflux for 18h. The solvent was removed in vacuo and the residue in water (200 ml) was extracted with EA (4×200 ml). The combined extracts were washed with brine (200 ml), dried and evaporated to give an oil (10.2 g) which was purified by chromatography on silica. Elution with ether and then 3:97 methanol-ether gave a solid (4.8 g). A portion was crystallised from ether-PE to give the title compound, m.p. 83°–84°.

The following Compound (Intermediate 9f) was prepared in similar manner:

(3aα,4α,5β,6aα)-(±)-Hexahydro-4-(hexahydro-1,4-oxazepin-4-yl)-5-[(tetrahydro-2H-pyran-2-yl)oxy]-2H-cyclopenta(b)furan-2-one m.p. 68.5°–72.5° from Intermediate 9d. Purification by chromatography using 85:15 ether-methanol as eluent.

INTERMEDIATE 9

(3aα,4α,5β,6aα)-(±)-Hexahydro-5-[(tetrahydro-2H-pyran-2-yl)oxy]-4-(4-thiomorpholinyl)-2H-cyclopenta(b)furan-2-ol Dibal (1.4 M in hexane; 20 ml) was added dropwise to a stirred solution of Intermediate 9e (4.7 g) in dry $CH_2Cl_2$ (100 ml) under nitrogen at −70°. After 2h methanol (100 ml) was cautiously added and the mixture allowed to warm to ambient temperature. After 2.5h, the mixture was filtered and the filtrate was evaporated. The residue was dissolved in $CH_2Cl_2$ (150 ml), dried and evaporated to give the title compound as an oil (4.25 g).

TLC 9:1 benzene-methanol $R_f$ 0.25.

INTERMEDIATE 10

(3aα,4α,5β,6aα)-(±)-Hexahydro-4-(hexahydro-1,4-oxazepin-4-yl)-5-[(tetrahydro-2H-pyran-2-yl)oxy]-2H-cyclopenta(b)furan-2-ol Prepared from Intermediate 9f in a similar manner to the preparation of Intermediate 9. TLC (B) $R_f$ 0.31.

INTERMEDIATE 11

[1α(Z),2β,3α,5α]-(±)-Methyl 7-[5-[[(1,1'-Biphenyl)-4-yl]methoxy]-3-hydroxy-2-(4-thiomorpholinyl)cyclopentyl]-5-heptenoate To a stirred solution of potassium t-butoxide (5.66 g) in dry THF (50 ml) under dry nitrogen was added (4-carboxybutyl)triphenylphosphonium bromide (11.2 g) and the mixture stirred at ambient temperature for 15 min. A solution of Intermediate 9 (2.77 g) in THF (25 ml) was added and stirring maintained for a further 1h. Water (10 ml) was added and the solvent was removed in vacuo. A solution of the residue in water (50 ml) was adjusted to pH 10 with 2 N NaOH and extracted with EA (3×30 ml). The aqueous layer was adjusted to pH 6 with phosphate buffer and extracted with EA (4×50 ml). The combined extracts were washed with brine, dried and treated with ethereal diazomethane. Concentration gave an oil which was chromatographed (L) to give the title compound (2.89 g). TLC (L) $R_f$ 0.35.

INTERMEDIATE 12

[1α(Z),2β,3α,5α]-(±)-Methyl 7-[5-Acetyloxy-2-(hexahydro-1,4-oxazepin-4-yl)-3-[(tetrahydro-2H-pyran-2-yl)oxy]cyclopentyl]-5-heptenoate To a stirred solution of potassium t-butoxide (3.36 g) in dry THF (30 ml) under dry nitrogen was added (4-carboxybutyl)triphenylphosphonium bromide (6.65 g) and the mixture stirred at ambient temperature for 15 min. A solution of Intermediate 10 (1.58 g) in THF (10 ml) was added and stirring maintained for a further 2h at 0°. The mixture was poured into water (50 ml) and the THF removed in vacuo. The residual solution was adjusted to pH 6 with phosphate buffer and extracted with $CH_2Cl_2$ (3×100 ml). The combined extracts were dried and treated with ethereal diazomethane. Concentration gave an oil which was dissolved in pyridine (29 ml) and treated with acetic anhydride (14.5 ml) at 0°. The solution was stirred at ambient temperature for 22h. The solvents were evaporated and the residue in 8% $NaHCO_3$ (250 ml) was extracted with $CH_2Cl_2$ (3×100 ml). The combined extracts were dried and evaporated and the residue purified by chromatography (L) to give the title compound as an oil (1.12 g). TLC (L) $R_f$ 0.35.

INTERMEDIATE 13

[1α(Z),2β,3α,5α]-(±)-Methyl 7-[2-(Hexahydro-1,4-oxazepin-4-yl)-5-hydroxy-3-[(tetrahydro-2H-pyran-2-yl)oxy]cyclopentyl]-5-heptenoate A solution of Intermediate 12 (1.12 g) in dry MeOH (20 ml) containing anhydrous $K_2CO_3$ (0.44 g) was stirred at ambient temperature for 16h. The mixture was poured into pH 6 phosphate buffer (50 ml) and extracted with $CH_2Cl_2$ (3×50 ml). The combined extracts were dried and evaporated to give the title compound as an oil (1.02 g).

TLC (B) $R_f$ 0.53.

INTERMEDIATE 14

(a) [1α(Z),2β,3α,5α]-(±)-Methyl 7-[5-[[(1,1'-Biphenyl)-4-yl]methoxy]-3-hydroxy-2-(4-thiomorpholinyl)cyclopentyl]-5-heptenoate To a stirred solution of Intermediate 11 (2.7 g) and NaH (46% dispersion in oil, 1.32 g) in dry DMF (20 ml) under nitrogen at 0° was added (bromomethyl)-1,1'-biphenyl (6.25 g). After 3h at 20° the mixture was carefully poured into pH 6 phosphate buffer (100 ml) and extracted with $CH_2Cl_2$ (4×50 ml). The combined extracts were washed with water (2×100 ml) dried and evaporated. The residue in 9:1 methanol-sulphuric acid (50 ml) was stirred at 20° for 0.5h. The solution was poured cautiously into 8% $NaHCO_3$ solution (150 ml) and extracted with $CH_2Cl_2$ (4×50 ml). The combined extracts were washed with water (2×50 ml), dried and evaporated, and the residue was purified by chromatography (K) followed by (L) to give the title compound (1.6 g).

TLC (L) $R_f$ 0.33.

The following compounds were prepared by a similar procedure:

(b) [1α(Z),2β,3α,5α]-(±)-Methyl 7-[5-[[(1,1'-Biphenyl)-4-yl]methoxy]-3-hydroxy-2-(4-thiomorpholinyl)cyclopentyl]-5-heptenoate, S-dioxide from Intermediate 7. Purification by chromatography (M).

TLC (M) $R_f$ 0.36.

(c) [1α(Z),2β,3α,5α]-(±)-Methyl 7-[5-[[(1,1'-Biphenyl)-4-yl]methoxy]-2-(hexahydro-1,4-oxazepin-4-yl)-3-hydroxycyclopentyl]-5-heptenoate from Intermediate 13. Purification by chromatography (L) followed by (F).

TLC (F) $R_f$ 0.18.

INTERMEDIATE 15

[1α(E),2β,3α,5α]-(±)-Methyl 7-[5-[[(1,1'-Biphenyl)-4-yl]methoxy]-3-hydroxy-2-(1-piperidinyl)cyclopentyl]-5-heptenoate A solution of Intermediate 2 (0.4 g) and p-toluenesulphinic acid (0.19 g) in dry 1,4-dioxan (15 ml) was heated under reflux under dry nitrogen for 5h. The solution was poured into 8% $NaHCO_3$ solution (45 ml) and extracted with EA (3×45 ml). The combined extracts were evaporated and the residue (GLC, Z/E 17:83) was purified by chromatography (B) to give the title compound as an oil (0.3 g).

GLC, Z/E 11:89.

IR ($CHBr_3$) 3580(br.), 1730 $cm^{-1}$

INTERMEDIATE 16

(a) [1α(Z),2β,3α,5α]-(±)-7-[5-[[(1,1'-Biphenyl)-4-yl]methoxy]-3-hydroxy-2-(1-piperidinyl)cyclopentyl]-5-heptenoic acid A suspension of Intermediate 2 (1.0 g) in methanol (6 ml) and water (2 ml) containing KOH (0.23g) was stirred at ambient temperature for 1-2 days. The mixture was evaporated to dryness and the residue in water (15 ml) was adjusted to pH 6.5 with 2 M NaHSO$_4$ solution. The solution was extracted with CH$_2$Cl$_2$ (3×15 ml) and the combined extracts were dried and evaporated to give the title compound as a foam (0.9 g).

TLC (H) R$_f$ 0.3.

The following compounds were prepared by a similar procedure:

(b)
[1α(Z),2β,3α,5α]-(±)-7-[5-[[(1,1'-Biphenyl)-4-yl]methoxy]-3-hydroxy-2-(4-thiomorpholinyl)cyclopentyl]-5-heptenoic acid m.p. 115°–117° from Intermediate 14a.

(c)
[1α(Z),2β,3α,5α]-(±)-7-[5-[[(1,1'-Biphenyl)-4-yl]methoxy]-2-(hexahydro-1,4-oxazepin-4-yl)-3-hydroxycyclopentyl]-5-heptenoic acid from Intermediate 14c. TLC (B) R$_f$ 0.11.

(d)
[1α(E),2β,3α,5α]-(±)-7-[5-[[(1,1'-Biphenyl)-4-yl]methoxy]-3-hydroxy-2-(1-piperidinyl)cyclopentyl]-5-heptenoic acid from Intermediate 15. I.R. (CHBr$_3$) 3580(br.), 1715(br.) cm$^{-1}$.

INTERMEDIATE 17

(a)
[1α(Z),2β,3α,5α]-(±)-7-[3-Hydroxy-5-[[4'-methyl-(1,1'-biphenyl)-4-yl]methoxy]-2-(4-morpholinyl)cyclopentyl]-5-heptenamide A stirred suspension of Intermediate 4 (1.5 g) in acetone (15 ml) was treated with triethylamine (1.6 ml). The solution was cooled to −10° and isobutyl chloroformate (1.3 ml) was added. Stirring was maintained for a further 0.5h, whereupon liquid ammonia (8 ml) was added followed by the reaction mixture being ent temperature over 1h. After concentration, the residue was diluted with combined 90 ml) and extracted with EA. The extracts were dried and evaporated. The residue was chromatographed (A) to give the title compound as a foam (1.2 g).

TLC (A) R$_f$ 0.13.

The following compounds were prepared by a similar procedure:

(b)
[1α(Z),2β,3α,5α]-(±)-7-[3-Hydroxy-5-[[4'-methoxy-(1,1'-biphenyl)-4-yl]methoxy]-2-(4-morpholinyl)cyclopentyl)-5-heptenamide m.p. 76°–77° from Intermediate 5. Purification initially by chromatography (C) and then by crystallisation (EA-ether).

(c)
[1α(Z),2β,3α,5α]-(±)-7-[3-Hydroxy-2-(4-morpholinyl)-5-[(2-phenylthien-4-yl)methoxy]cyclopentyl]-5-heptenamide from Intermediate 6. Purification initially by chromatography on alumina (D) and then on silica (E).

TLC (E) R$_f$ 0.25.

(d)
[1α(Z),2β,3α,5α]-(±)-7-[5-[[(1,1'-Biphenyl)-4-yl]methoxy]-3-hydroxy-2-(1-piperidinyl)cyclopentyl]-5-heptenamide m.p. 94°–96° from Intermediate 16a. Purification by crystallisation (EA-PE).

(e)
[1α(Z),2β,3α,5α]-(±)-N-Methyl-7-[5-[[(1,1'-biphenyl)-4-yl]methoxy]-3-hydroxy-2-(1-piperidinyl)cyclopentyl]-5-heptenamide from Intermediate 16a and methylamine. Purification by chromatography (C).

TLC (C) R$_f$ 0.32.

(f)
[1α(Z),2β,3α,5α]-(±)-N-Methyl-7-[3-hydroxy-5-[[4'-methoxy(1,1'-biphenyl)-4-yl]methoxy]-2-(4-morpholinyl)cyclopentyl]-5-heptenamide from Intermediate 5 and methylamine. Purification by chromatography (B).

TLC (B) R$_f$ 0.14.

(g)
[1α(Z),2β,3α,5α]-(±)-N-Methyl-7-[5-[[(1,1'-biphenyl)-4-yl]methoxy]-3-hydroxy-2-(4-morpholinyl)cyclopentyl]-5-heptenamide from Intermediate 1 and methylamine. Purification by chromatography (A).

TLC (A) R$_f$ 0.18.

(h)
[1α(Z),2β,3α,5α]-(±)-N-(2-Methoxyethyl)-7-[5-[[(1,1'-biphenyl)-4-yl]methoxy]-3-hydroxy-2-(4-morpholinyl)cyclopentyl]-5-heptenamide from Intermediate 1 and 2-methoxyethylamine. Purification by chromatography (C).

TLC (C) R$_f$ 0.3.

(i)
[1α(Z),2β,3α,5α]-(±)-7-[5-[[(1,1'-Biphenyl)-4-yl]methoxy]-3-hydroxy-2-(4-thiomorpholinyl)cyclopentyl]-5-heptenamide m.p. 88°–90° from Intermediate 16b in acetonitrile. Purification initially by chromatography (F) followed by (B), and then by crystallisation (EA-PE).

(j)
[1α(Z),2β,3α,5α]-(±)-7-[5-[[(1,1'-Biphenyl)-4-yl]methoxy]-2-(hexahydro-1,4-oxazepin-4-yl)-3-hydroxycyclopentyl]-5-heptenamide from Intermediate 16c in acetonitrile. Purification by precipitation at 0° from ether-PE.

TLC (B) R$_f$ 0.24.

(k)
[1α(E),2β,3α,5α]-(±)-7-[5-[[(1,1'-Biphenyl)-4-yl]methoxy]-3-hydroxy-2-(1-piperidinyl)cyclopentyl]-5-heptenamide from Intermediate 16d in acetonitrile. Purification by chromatography on alumina (F).

TLC Alumina (F) R$_f$ 0.3.

(l)

[1α(Z),2β,3α,5α]-(±)-7-[3-Hydroxy-2-(4-morpholinyl)-5-[4-(thien-2-yl)phenylmethoxy]cyclopentyl]-5-heptenamide from Intermediate 8 in acetonitrile. Purification by chromatography (B).
TLC (B) R_f 0.1.

(m) [1α(Z),2β,3α,5α]-(±)-Methyl N-[7-[5-[[(1,1'-Biphenyl)-4-yl]methoxy]-3-hydroxy-2-(4-morpholinyl)cyclopentyl]-1-oxo-5-heptenyl]glycinate from Intermediate 1 and glycine methyl ester, hydrochloride. Purification by chromatography (C).
TLC (C) R_f 0.43.

INTERMEDIATE 18

[1α(Z),2β,3α,5α]-(±)-7-[5-[[(1,1'-Biphenyl)-4-yl]methoxy]-3-hydroxy-2-(4-thiomorpholinyl)cyclopentyl]-5-heptenamide, S-dioxide A solution of Intermediate 14b (1.2 g) in anhydrous MeOH (25 ml) and liquid ammonia (25 ml) was heated at 120° for 36h. The solvents were evaporated and the residue purified by chromatography (B) to give the title compound as a foam (0.88 g).
TLC (B) R_f 0.33.

INTERMEDIATE 19

[1α(Z),2β,3α,5α]-(±)-N-[7-[5-[[(1,1'-Biphenyl)-4-yl]methoxy]-3-hydroxy-2-(4-morpholinyl)cyclopentyl]-1-oxo-5-heptenyl]glycine A solution of Intermediate 17 m (0.5 g) and K_2CO_3 (0.14 g) in water (7 ml) and MeOH (9 ml) was heated under reflux for 5h. The mixture was diluted with pH 6.5 phosphate buffer (100 ml) and extracted with EA (6×100 ml). The combined extracts were dried and evaporated to give the title compound as a foam (0.43 g).
TLC (O) R_f 0.35.

EXAMPLE 1

(a)

[1α(Z),2β,5α]-(±)-7-[5-[[(1,1'-Biphenyl)-4-yl]methoxy]-2-(4-morpholinyl)-3-oxocyclopentyl]-5-heptenamide, compound with ethyl acetate (3:1)

A stirred suspension of Intermediate 3 (0.5 g) in acetone (10 ml) was treated with triethylamine (0.29 ml). The solution produced was cooled to −10° and isobutyl chloroformate (0.28 ml) was added. Stirring was maintained for a further 15 min, whereupon liquid ammonia (10 ml) was added. After 45 min at −10° the solution was poured into pH 6.5 phosphate buffer (50 ml) and extracted with CH_2Cl_2 (3×50 ml). The combined extracts were dried and evaporated and the residue was purified initially by chromatography (J) and then by crystallisation (EA-PE) to give the title compound (0.4 g), m.p. 78°–79.5°.
I.R. (CHBr_3) 3520, 3400, 1738, 1675 cm$^{-1}$.

The following compound was prepared by a similar procedure:

(b)

[1α(Z),2β,5α]-(±)-N-(3-Methoxypropyl)-7-[5-[[(1,1'-biphenyl)-4-yl]methoxy]-2-(4-morpholinyl)-3-oxocyclopentyl]-5-heptenamide m.p. 51°–52° from Intermediate 3 and 3-methoxypropylamine in acetonitrile. Purification initially by chromatography (F) then by crystallisation (ether-PE).
TLC (F) R_f 0.48.

EXAMPLE 2

(a)

[1α(Z),2β,5α]-(±)-7-[5-[[4'-Methyl(1,1'-biphenyl)-4-yl]methoxy]-2-(4-morpholinyl)-3-oxocyclopentyl]-5-heptenamide Pyridine-sulphur trioxide complex (1.2 g) in DMSO (7 ml) was added to a stirred solution of Intermediate 17a (0.93 g) in CH_2Cl_2 (7 ml), DMSO (4 ml) and triethylamine (2.3 ml) and stirring continued for a further 1h at 20°. The mixture was diluted with water (100 ml) and extracted with EA (3×40 ml). The combined extracts were washed with water (2×60 ml), dried and evaporated. The residue was chromatographed (B) to give the title compound which was crystallised twice from EA-PE (b.p. 60°–80°), (0.29 g), m.p. 99°–102°.

Analysis Found: C, 73.3; H, 7.7; N, 5.6; C_30H_38N_2O_4 requires: C, 73.4; H, 7.8; N, 5.7%.

The following compounds were prepared by a similar procedure:

(b)

[1α(Z),2β,5α]-(±)-7-[5-[[4'-Methoxy(1,1'-biphenyl)-4-yl]methoxy]-2-(4-morpholinyl)-3-oxocyclopentyl]-5-heptenamide, compound with ether (2:1)

m.p. 84°–85° from Intermediate 17b. Purification initially by chromatography (B) and then by crystallisation (B).

Analysis Found: C, 70.3; H, 7.7; N, 5.1; C_30H_38N_2O_5.0.5C_4H_10O requires: C, 70.7; H, 8.0; N, 5.2%.

(c)

[1α(Z),2β,5α]-(±)-7-[2-(4-Morpholinyl)-3-oxo-5-[(2-phenylthien-4-yl)methoxy]cyclopentyl]-5-heptenamide from Intermediate 17c. Purification by chromatography (F).
TLC (F) R_f 0.3.
I.R. (CHBr_3) 3520, 3400, 1740, 1678 cm$^{-1}$.

(d)

[1α(Z),2β,5α]-(±)-7-[5-[[(1,1'-Biphenyl)-4-yl]methoxy]-3-oxo-2-(1-piperidinyl)cyclopentyl]-5-heptenamide m.p. 87°–90°, from Intermediate 17d. Purification initially by chromatography (G) and then by crystallisation (EA-ether-PE).

Analysis Found: C, 75.9; H, 8.05; N, 5.85; C_30H_38N_2O_3 requires C, 75.9; H, 8.1; N, 5.9%

(e)

[1α(Z),2β,5α]-(±)-N-Methyl-7-[5-[[(1,1'-biphenyl)-4-yl]methoxy]-3-oxo-2-(1-piperidinyl)cyclopentyl]-5-heptenamide m.p. 94°–96°, from Intermediate 17e. Purification by chromatography (F).
TLC (F) R_f 0.44.

(f)

[1α(Z),2β,5α]-(±)-N-Methyl-7-[5-[[4'-methoxy(1,1'-biphenyl)-4-yl]methoxy]-2-(4-morpholinyl)-3-oxocyclopentyl]-5-heptenamide from Intermediate 17f. Purification by chromatography (B).

TLC (B) R$_f$ 0.47.

Analysis Found: C, 70.5; H, 7.9; N, 5.3; $C_{31}H_{40}N_2O_5$ requires: C, 70.8; H. 7.9; N, 5.5%.

(g)

[1α(Z),2β,5α]-(±)-N-(2-Methoxyethyl)-7-[5-[[(1,1'-biphenyl)-4-yl]methoxy]-2-(4-morpholinyl)-3-oxocyclopentyl]-5-heptenamide m.p. 73.5°–74° from Intermediate 17h. Purification by chromatography (L) followed by (B).

Analysis Found: C, 71.9; H, 7.9; N, 5.1; $C_{32}H_{42}N_2O_5$ requires: C, 71.9; H, 7.9; N, 5.2%.

(h)

[1α(Z),2β,5α]-(±)-7-[5-[[(1,1'-Biphenyl)-4-yl]methoxy]-3-oxo-2-(4-thiomorpholinyl)cyclopentyl]-5-heptenamide from Intermediate 17i. Purification by chromatography (F).

TLC (F) R$_f$ 0.59.

I.R. (CHBr$_3$) 3510, 3400, 1740, 1680, 1590 cm$^{-1}$.

(i)

[1α(Z),2β,5α]-(±)-7-[5-[[(1,1'-Biphenyl)-4-yl]methoxy]-3-oxo-2-(4-thiomorpholinyl)cyclopentyl]-5-heptenamide, S-dioxide m.p. 120°–122° from Intermediate 18. Purification initially by chromatography (E) and then by crystallisation (EA).

Analysis Found: C, 66.1; H, 6.9; N, 5.2; $C_{29}H_{36}N_2O_5S$ requires: C, 66.4; H, 6.9; N, 5.3%.

(j)

[1α(Z),2β,5α]-(±)-7-[5-[[(1,1'-Biphenyl)-4-yl]methoxy]-2-(hexahydro-1,4-oxazepin-4-yl)-3-oxocyclopentyl]-5-heptenamide from Intermediate 17j. Purification by chromatography (B).

TLC (B) R$_f$ 0.32.

IR (CHBr$_3$) 3525, 3405, 1740, 1680, 1580 cm$^{-1}$.

(k)

[1α(E),2β,5α]-(±)-7-[5-[[(1,1'-Biphenyl)-4-yl]methoxy]-3-oxo-2-(1-piperidinyl)cyclopentyl]-5-heptenamide from Intermediate 17k. Purification by chromatography (F).

TLC (F) R$_f$ 0.24.

I.R. (CHBr$_3$) 3520, 3405, 1735, 1678, 1590 cm$^{-1}$.

(l)

[1α(Z),2β,5α]-(±)-7-[2-(4-Morpholinyl)-3-oxo-5-[(4-thien-2-yl)phenylmethoxy]cyclopentyl]-5-heptenamide from Intermediate 17l. Purification by chromatography (B). m.p. 100°–101°.

Analysis Found: C, 66.95; H, 7.1; N, 5.7; $C_{27}H_{34}N_2O_4S$ requires: C, 67.2; H, 7.1; N 5.8%.

(m)

[1α(Z),2β,5α]-(±)-N-[7-[5-[[(1,1'-Biphenyl)-4-yl]methoxy]-2-(4-morpholinyl)-3-oxocyclopentyl]-1-oxo-5-heptenyl]glycine, compound with piperazine (1:1)

m.p. 82.5°–87° from Intermediate 19. Purification initially by chromatography (N) and then by precipitation from ether-EA as the piperazine (1:1) salt.

TLC (as acid) (N) R$_f$ 0.62.

EXAMPLE 3

(a)

(1α,2β,5α)-(±)-5-[[4'-Methyl(1,1'-biphenyl)-4-yl]methoxy]-2-(4-morpholinyl)-3-oxocyclopentaneheptanamide A solution of the product of Example 2a (0.36 g) in EA (20 ml) was hydrogenated over 10% palladium oxide on charcoal (0.2 g). Removal of the catalyst by filtration and the solvent by evaporation gave a solid which was purified from EA-PE-ether to give the title compound (0.31 g), m.p. softens >93° melts 109°–111°.

Analysis Found: C, 72.8; H, 8.4; N, 5.6; $C_{30}H_{40}N_2O_4$ requires: C, 73.1; H, 8.2; N, 5.7%

The following compound was prepared by a similar procedure:

(b)

(1α,2β,5α)-(±)-5-[[(1,1'-Biphenyl)-4-yl]methoxy]-3-oxo-2-(1-piperidinyl)cyclopentaneheptanamide m.p. 96°–98° from the product of Example 2d. Purification by chromatography (L).

Analysis Found: C, 75.3; H, 8.4; N, 5.9; $C_{30}H_{40}N_2O_3$ requires: C, 75.6; H, 8.5; N, 5.9%

EXAMPLE 4

[1α(Z),2β,5α]-(±)-N-Methyl-7-[5-[[(1,1'-biphenyl)-4-yl]methoxy]-2-(4-morpholinyl)-3-oxocyclopentyl]-5-heptenamide DMSO (0.49 ml) was added dropwise to a cooled (−78°), stirred solution of oxalyl chloride (0.3 ml) in CH$_2$Cl$_2$ (10 ml) under nitrogen. After ca. 10 min. a solution of Intermediate 17 g (0.67 g) in CH$_2$Cl$_2$ (20 ml) was added over 0.5h. After a further 1h triethylamine (2.84 ml) was added at −78°. The cooling bath was removed and the mixture attained ambient temperature over 1h. The mixture was diluted with 8% NaHCO$_3$ solution and CH$_2$Cl$_2$. The organic layer was separated, dried and evaporated and the residue was purified by chromatography (F) to give the title compound (0.53 g), m.p. 94°–96°, Analysis Found: C, 73.3; H, 7.8; N, 5.6; $C_{30}H_{38}N_2O_4$ requires: C, 73.4; H, 7.8; N, 5.7%

PHARMACEUTICAL EXAMPLES

Tablets

These may be prepared by direct compression or wet granulation. The direct compression method is preferred but may not be suitable in all cases as it is dependent upon the dose level and physical characteristics of the active ingredient.

| A. Direct Compression | mg/tablet |
|---|---|
| Active ingredient | 100.00 |
| Microcrystalline Cellulose B.P.C. | 298.00 |
| Magnesium Stearate | 2.00 |

-continued

| A. Direct Compression | mg/tablet |
|---|---|
| Compression Weight | 400.00 |

The active ingredient is sieved through a 250 m$^{-6}$ sieve, blended with the excipients and compressed using 10.0 mm punches. Tablets of other strengths may be prepared by altering the compression weight and using punches to suit.

| B Wet granulation | mg/tablet |
|---|---|
| Active ingredient | 100.00 |
| Lactose B.P. | 238.00 |
| Starch B.P. | 40.00 |
| Pregelatinised Maize Starch B.P. | 20.00 |
| Magnesium Stearate B.P. | 2.00 |
| Compressed Weight | 400.00 |

The active ingredient is sieved through a 250 m$^{-6}$ sieve and blended with the lactose, starch and pregelatinised starch. The mixed powders are moistened with purified water, granules are made, dried, screened and blended with the magnesium stearate. The lubricated granules are compressed into tablets as described for the direct compression formulae.

The tablets may be film coated with suitable film forming materials, e.g. methyl cellulose or hydroxylpropyl methyl cellulose using standard techniques. Alternatively the tablets may be sugar coated.

Capsules

| | mg/capsule |
|---|---|
| Active ingredient | 100.00 |
| *STA-RX 1500 | 99.00 |
| Magnesium Stearate B.P. | 1.00 |
| Fill Weight | 200.00 mg |

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

Suspensions

| | mg/5ml dose |
|---|---|
| Active ingredient | 100.0 |
| Aluminium monostearate | 75.0 |
| Sucrose (powdered) | 125.0 |
| Flavour | as |
| Colour | required |
| Fractionated coconut oil to | 5.00ml. |

The aluminium monostearate is dispersed in about 90% of the fractionated coconut oil. The resulting suspension is heated to 115° C. while stirring and then cooled. The flavour and colour are added and the active ingredient and sucrose are suitably dispersed. The suspension is made up to volume with the remaining fractionated coconut oil and mixed.

Injection for Intravenous Administration

| Active ingredient | 50 mg |
|---|---|
| Suitable vehicle to | 5 ml. |

A sterile presentation of the active ingredient in an ampoule or vial together with an ampoule containing a suitable vehicle. The former may be prepared by (a) filling sterile material into vials under aseptic conditions (b) freeze drying a sterile solution of the active ingredient under aseptic conditions.

The vehicle may be (a) Water for Injections B.P. (b) Water for Injections B.P. containing: (1) sodium chloride to adjust the tonicity of the solution and/or (2) buffer salts or dilute acid or alkali to facilitate solution of the active ingredient.

The vehicle is prepared, clarified and filled into appropriate sized ampoules sealed by fusion of the glass. The vehicle is sterilised by heating in an autoclave using one of the acceptable cycles.

We claim:

1. Compounds of the general formula (1)

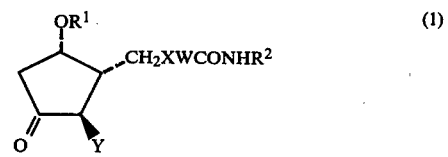

wherein
R$^1$ is (i) straight or branched C$_{1-5}$ alkyl substituted by (a) phenyl optionally substituted by C$_{1-6}$ alkyl, C$_{5-7}$ cycloalkyl, phenylalkyl having a C$_{1-3}$ alkyl portion, thienyl or phenyl (optionally substituted by C$_{1-4}$ alkyl, C$_{1-4}$ alkoxy or phenyl), (b) thienyl optionally substituted by C$_{1-6}$ alkyl, C$_{1-6}$ alkoxy, C$_{5-7}$ cycloalkyl or phenyl (optionally substituted by C$_{1-3}$ alkyl, C$_{1-3}$ alkoxy or halogen), or (c) naphthyl (optionally substituted by C$_{1-4}$ alkyl or C$_{1-4}$ alkoxy), or (ii) cinnamyl;

R$^2$ is a hydrogen atom, a methyl group, —(CH$_2$)$_n$OR$^3$ (where n is 2-5 and R$^3$ is C$_{1-4}$ alkyl) or —CHR$^4$(CH$_2$)$_m$COOH (where R$^4$ is a hydrogen atom or a methyl group and m is 0-2);

W is straight or branched C$_{1-7}$ alkylene;

X is cis or trans —CH=CH— or —CH$_2$CH$_2$—;

Y is a saturated heterocyclic amino group (attached to the cyclopentane ring via the nitrogen atom) which has 5-8 ring members and (a) optionally contains in the ring —O—, —S—, —SO$_2$—, or —NR$^5$ (where R$^5$ is a hydrogen atom, C$_{1-7}$ alkyl or aralkyl having a C$_{1-4}$ alkyl portion); or (b) is optionally substituted by one or more C$_{1-4}$ alkyl groups; and the physiologically acceptable salts and solvates thereof.

2. Compounds as claimed in claim 1 in which Y is morpholino, piperidino, homomorpholino, thiamorpholino or 1,1-dioxothiamorpholino.

3. Compounds as claimed in claim 1 in which X is cis—CH=CH—.

4. Compounds as claimed in claim 1 in which W is —CH$_2$CH$_2$CH$_2$—.

5. Compounds as claimed in claim 1 in which R$^2$ is a hydrogen atom.

6. Compounds as claimed in claim 5 in which $R^1$ is a substituted or unsubstituted phenyl ($C_{1-3}$) alkyl or naphthyl group as defined in claim 1 (other than a thienylphenylalkyl group) and X is cis or trans —CH=CH—.

7. Compounds as claimed in claim 1 in which $R^1$ is phenyl ($C_{1-3}$) alkyl in which the phenyl group is substituted by thienyl or phenyl, the latter phenyl group being optionally substituted by $C_{1-4}$ alkyl or $C_{1-4}$ alkoxy, or is a phenylthienylalkyl group in which the alkyl portion contains 1-3 carbon atoms.

8. Compounds as claimed in claim 1 in which:

W is —CH$_2$CH$_2$CH$_2$—,
X is cis —CH=CH—,
Y is morpholino or piperidino,
$R^1$ is benzyl in which the phenyl group is substituted by phenyl, tolyl, methoxyphenyl or thienyl and
$R^2$ is a hydrogen atom
and the physiologically acceptable salts and solvates thereof.

9. A pharmaceutical composition comprising a compound as claimed in claim 1 and one or more pharmaceutical carriers.

* * * * *

UNITED STATES PATENT AND TRADEMARK OFFICE
CERTIFICATE OF CORRECTION

PATENT NO. : 4,371,530

DATED : February 1, 1983

INVENTOR(S) : Collington et al.

It is certified that error appears in the above-identified patent and that said Letters Patent is hereby corrected as shown below:

Column 17, line 42 "ent" should be "allowed to rise to ambient"

Signed and Sealed this

Twentieth Day of September 1983

[SEAL]

Attest:

GERALD J. MOSSINGHOFF

Attesting Officer

Commissioner of Patents and Trademarks